(12) United States Patent
Borkovec et al.

(10) Patent No.: US 10,588,349 B2
(45) Date of Patent: Mar. 17, 2020

(54) ELECTRONIC SMOKING DEVICE

(71) Applicant: Fontem Holdings 1 B.V., Amsterdam (NL)

(72) Inventors: Vaclav Borkovec, Hamburg (DE); Stefan Biel, Hamburg (DE)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 158 days.

(21) Appl. No.: 15/566,137

(22) PCT Filed: Apr. 11, 2016

(86) PCT No.: PCT/EP2016/057893
§ 371 (c)(1),
(2) Date: Oct. 12, 2017

(87) PCT Pub. No.: WO2016/166049
PCT Pub. Date: Oct. 20, 2016

(65) Prior Publication Data
US 2018/0110263 A1    Apr. 26, 2018

(30) Foreign Application Priority Data
Apr. 15, 2015   (EP) ..................... 15163660

(51) Int. Cl.
*A24F 47/00* (2006.01)
*A61M 15/06* (2006.01)
*A61M 11/04* (2006.01)
*H05B 3/44* (2006.01)
*A61M 16/00* (2006.01)

(52) U.S. Cl.
CPC .......... *A24F 47/008* (2013.01); *A24F 47/004* (2013.01); *A61M 11/042* (2014.02); *A61M 15/06* (2013.01); *H05B 3/44* (2013.01); *A61M 2016/0024* (2013.01); *A61M 2016/0039* (2013.01); *A61M 2205/3375* (2013.01);
(Continued)

(58) Field of Classification Search
CPC ..................................................... A24F 47/008
See application file for complete search history.

(56) References Cited

U.S. PATENT DOCUMENTS 9,072,322 B2    7/2015  Liu
9,197,726 B2 *  11/2015 Stanimirovic ........ H04M 1/215
(Continued)

FOREIGN PATENT DOCUMENTS

CN    104010528 A    8/2014
WO    2015/086318 A1  6/2015

*Primary Examiner* — James Harvey
(74) *Attorney, Agent, or Firm* — Dykema & Gossett PLLC

(57) ABSTRACT

An electronic smoking device (1) includes a housing (2), a receiving unit (3) for the reception of a solid smoking material (4) and a primary heating element (5). The primary heating element and the receiving unit are arranged adjacent to one another. The electronic smoking device further comprises a positioning element for forcing solid smoking material inserted in the receiving unit towards the primary heating element. Solid smoking material within the receiving unit which is forced towards the primary heating element by the positioning element is liquefied and atomized by the primary heating element. The receiving unit, the primary heating element and the positioning element are arranged within the housing.

16 Claims, 9 Drawing Sheets

(52) U.S. Cl.
CPC ............... *A61M 2205/3653* (2013.01); *A61M 2205/584* (2013.01); *A61M 2205/8206* (2013.01)

(56) References Cited

U.S. PATENT DOCUMENTS

| | | |
|---|---|---|
| 2013/0160764 A1 | 6/2013 | Liu |
| 2014/0041655 A1 | 2/2014 | Barron et al. |
| 2014/0216483 A1 | 8/2014 | Alima |
| 2016/0213066 A1* | 7/2016 | Zitzke .................. A24F 47/008 |
| 2016/0262457 A1* | 9/2016 | Borkovec ............. A24F 47/008 |
| 2018/0110263 A1* | 4/2018 | Borkovec ............. A61M 15/06 |
| 2018/0132523 A1* | 5/2018 | Biel ....................... A24F 47/008 |
| 2018/0168231 A1* | 6/2018 | Reevell ............. A61M 15/0003 |
| 2019/0031407 A1* | 1/2019 | Biel .................... B65D 47/248 |

* cited by examiner

ELECTRONIC SMOKING DEVICE

CROSS-REFERENCE TO RELATED APPLICATIONS

This application claims priority to national stage filing based upon international application no. PCT/EP2016/057893, filed 11 Apr. 2016 and published in English on 20 Oct. 2016 under international publication no. WO/2016/166049 (the '893 application), which claims priority to European application no. 15163660.2, filed 15 Apr. 2015 (the '660 application). The '137 application, '893 application and the '660 application are all hereby incorporated by reference as though fully set forth herein.

FIELD OF INVENTION

The present invention relates generally to electronic smoking devices and in particular electronic cigarettes.

BACKGROUND OF THE INVENTION

An electronic smoking device, such as an electronic cigarette (e-cigarette), usually has a housing accommodating an electric power source (e.g. a single use battery or a rechargeable battery), and an electrically operable atomizer. The atomizer vaporizes or atomizes liquid supplied from a reservoir and provides vaporized or atomized liquid as an aerosol. Control electronics control the activation of the atomizer. In many electronic cigarettes, an airflow sensor is provided within the electronic smoking device which detects a user puffing on the device (e.g., by sensing an underpressure or an air flow pattern through the device). The airflow sensor indicates or signals the puff to the control electronics. Alternatively, a button may be used to switch on the electronic smoking device to generate a puff of flavor. When a puff is detected, the control electronics supplies electrical power to the atomizer thereby creating vaporized liquid as an aerosol.

Recently, electronic smoking devices which allow the consumption of a solid smoking material are increasingly capturing the market. The solid smoking material often consists of a wax or a gel which can comprise nicotine and/or further other flavoured or non-flavoured compositions. Within an electronic smoking device, the solid smoking material is first liquefied and then atomized by an atomizer. In order to charge the electronic smoking device with solid smoking materials, most devices known to the state of the art require the user to open the electronic smoking device and to insert the solid smoking material using tools such as spatulas or little scoops. Such a procedure is complicated, time-consuming and can unnecessarily interfere with the enjoyment of puffing on the device.

SUMMARY OF THE INVENTION

In accordance with one aspect of the present invention there is provided an electronic smoking device which comprises a housing and a receiving unit for the receiving solid smoking material suited for aerosol generation. The electronic smoking device further comprises a primary heating element which is arranged adjacent to the receiving unit. The primary heating element is adapted to liquefy solid smoking material and to atomize liquefied solid smoking material. Moreover, the electronic smoking device comprises a positioning element for forcing solid smoking material inserted in the receiving unit towards the primary heating element, wherein the receiving unit, the primary heating element and the positioning element are arranged within the housing.

An advantage of such an electronic smoking device is the amelioration in the handling of the solid smoking material. A user intending to charge the electronic smoking device with solid smoking material can easily insert solid smoking material into the receiving unit manually, without any need for further tools. The positioning element then forces the solid smoking material inserted in the receiving unit towards the primary heating element positioning the solid material in a consistent position for the generation of an aerosol and reducing the frequency with which the solid smoking material position needs to be adjusted or replaced.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
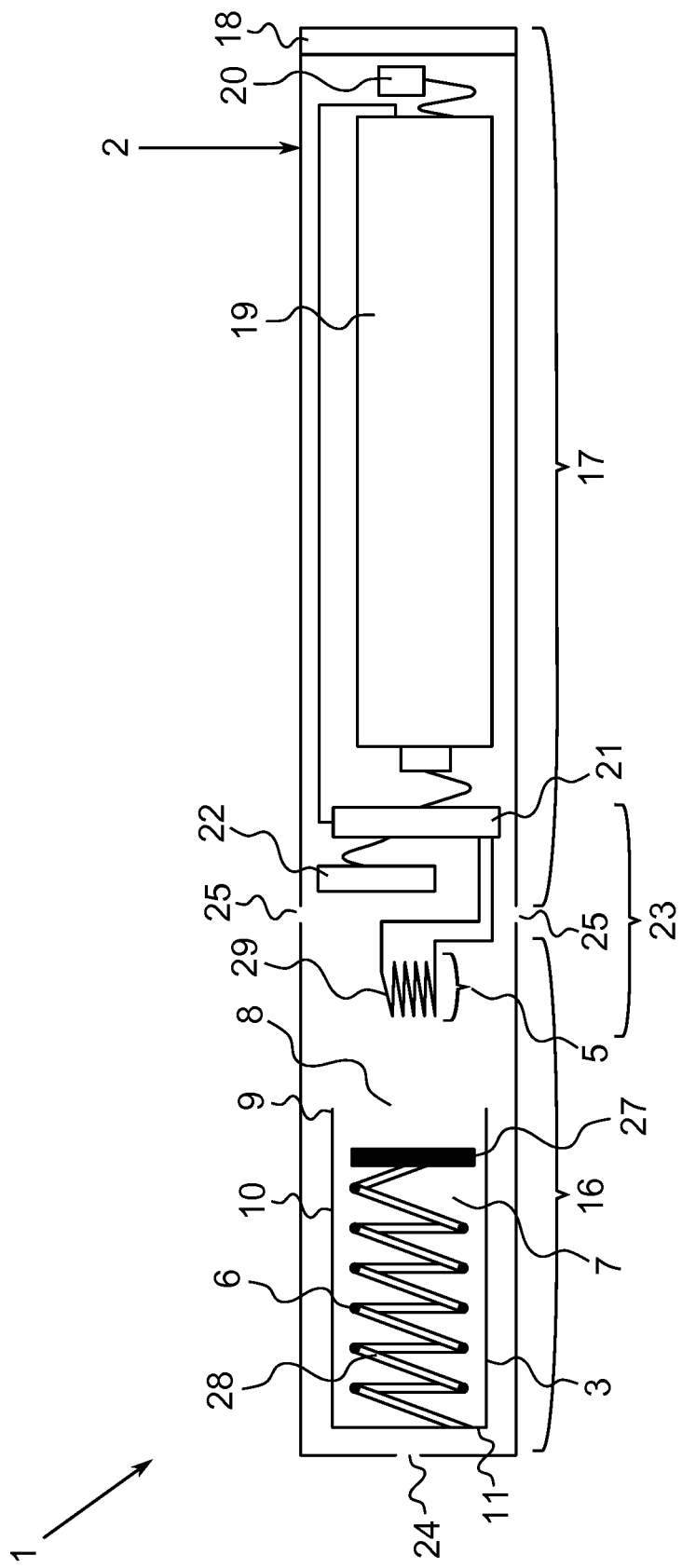
FIG. 1 is a schematic cross-sectional illustration of a first embodiment of an electronic smoking device according to the invention.

FIG. 1 shows a schematic cross-sectional illustration of a first embodiment of an electronic smoking device 1 according to the invention. In this first embodiment, the electronic smoking device 1 is realized as an e-cigarette 1 which comprises a cylindrical housing 2 having a main body 17 and a mouthpiece portion 16. Together the main body 17 and the mouthpiece portion 16 form a cylindrical tube which is approximately the same size and shape as a conventional cigarette. However, in other embodiments, electronic smoking devices 1 can be realized which can be larger than conventional cigarettes and which can have a shape that differs from the shape of a conventional cigarette.

The main body 17 and the mouthpiece portion 16 are typically made of steel or hardwearing plastic and act to provide a housing 2 to contain the operative elements of the electronic smoking device 1. In this embodiment of the electronic smoking device 1, the main body 17 and the mouthpiece portion 16 may be configured to fit together by means of a friction push fit. Alternatively in some electronic smoking devices 1, the main body 17 and mouthpiece portion 16 may be parts of a single integrally formed tube.

An end cap 18 is provided at the end of the main body 17 remote from the mouthpiece portion 16 enclosing that end of the main body 17. The end cap 18 is typically made from translucent plastic but is not restricted thereto.

A battery 19 is provided within the central cavity enclosed by the main body 17. Also contained within the central cavity defined by the main body 17 are a light emitting diode (LED) 20, control electronics 21 and an airflow sensor 22. The battery 19 is electrically connected to the LED 20 and the control electronics 21 and the airflow sensor 22 is connected to the control electronics 21. In this example the LED 20 is provided at one end of the main body 17, adjacent to the end cap 18 and the control electronics 21 and airflow sensor 22 are provided in the central cavity at the other end of the battery 19 adjacent the mouth piece portion 16.

The airflow sensor 22 acts as a puff detector, detecting a user puffing or sucking on the mouthpiece portion 16 of the electronic smoking devices 1. The airflow sensor 22 can be any suitable sensor for detecting changes in airflow or air pressure such as a microphone switch including a deformable membrane which is caused to move by variations in air pressure.

The control electronics 21 are also connected to an atomizer 23 which in this illustrative example comprises a primary heating element 5 which is exemplarily realized as heating coil 29 extending across at least a part of the diameter of the mouthpiece portion 16 of the electronic smoking device 1. The dimensions of the diameter of the mouthpiece portion 16 and of the primary heating element 5 are such that the primary heating element 5 does not completely block the airflow passage within the mouthpiece portion 16 but rather an air gap is provided either side of the heating coil 29 enabling air to flow past the primary heating element 5. An air inhalation port 24 is provided at the end of the mouthpiece portion 16 remote from the main body 17 of the electronic smoking device 1 and a pair of air inlets 25 are provided in the housing 2 at the intersection between the main body 17 and the mouthpiece portion 16 adjacent the airflow sensor 22. In other embodiments the air inlets 25 may be positioned in a different location and/or a single air inlet might be used or alternatively the housing 2 may not be air tight and air may enter the housing 2 without there being any explicit air inlets.

In this first embodiment of the invention, the electronic smoking device 1 further comprises a receiving unit 3 for receiving solid smoking material suited for aerosol generation. The receiving unit 3 is arranged within the mouthpiece portion 16 of the electronic smoking device 1 and comprises a hollow body 7 with an open end 8 that has a rim 9, side walls 10 extending from the rim 9 and a rear wall 11. In this first embodiment, the receiving unit 3 substantially has the shape of a tube which is closed via the rear wall 11. The open end 8 with the rim 9 at the opposite end of the receiving unit 3 to the rear wall 11 and faces the primary heating element 5 of the electronic smoking device 1 with the rear wall 11 of the receiving unit facing the air inhalation port 24 at the end of the mouthpiece portion 16 remote from the main body 17. However, the form of the receiving unit 3 is not restricted to the above described shape. The receiving unit 3 acts as a container or receptacle for receiving solid smoking material suited for aerosol generation. In some designs, the solid smoking material may optionally be held directly within the housing, without using a separate receiving unit.

The primary heating element 5 is arranged adjacent to the receiving unit 3 and adapted to liquefy solid smoking material and to atomize the then liquefied solid smoking material. The electronic smoking device 1 further comprises a positioning element 6 for forcing solid smoking material inserted in the receiving unit 3 towards the primary heating element 5, wherein the receiving unit 3, the primary heating element 5 and the positioning element 6 are arranged within the housing 2.

In this first embodiment, the positioning element 6 is exemplarily realized as a mechanical positioning element which comprises a piston 27 that is attached to a spring 28. However, it is also possible to carry out embodiments of electronic smoking devices 1 according to the invention which comprise other positioning elements 6 that are suited to force solid smoking material inserted in the receiving unit 3 towards the primary heating element 5. Such positioning elements 6 for example can be hydraulic means or electromechanical means or another mechanical element or unit, as for example a spring 28 without a piston 27 or the like. In some embodiments, the positioning element 6 is a part of the receiving unit 3. In such an embodiment, the shape of the positioning element 6 corresponds to the shape of the receiving unit 3. The use of only a spring 28 as a positioning element 6 is cost-efficient and reliably serves to move solid smoking material within the electronic smoking device to a position where the solid smoking material can be liquefied and atomized.

The electronic smoking device 1 according to the invention is designed for the consumption of a solid smoking material. Such a solid smoking material can be realized as a gel and/or a wax or it can be made at least in part of such a gel and/or such a wax. The gel and/or wax exemplarily can be pressed to a block or the like. The solid smoking material can be any material suitable for atomization which can be embedded in a carrier matrix or medium. Furthermore, the solid smoking material can comprise nicotine. In addition, flavored materials can be added to the solid smoking material, for example esters, such as isoamyl acetate, linalyl acetate, isoamyl propionate, linalyl butyrate and the like or natural essential oils as plant essential oils, such as spearmint, peppermint, cassia, jasmine and the like or animal essential oils, such as musk, amber, civet, castor and the like or simple flavoring materials, such as anethole, limonene, linalool, eugenol and the like or hydrophilic flavour components such as a leaf tobacco extract or natural plant flavoring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavored materials as mentioned above into new flavored materials. Moreover, it is possible to adsorb any flavor onto a solid smoking material and to use this solid smoking material as flavored material within an electronic smoking device 1 according to the present invention.

The solid smoking material is free from any components that need to be burned. Furthermore, the solid smoking material does not comprise tobacco fibres or reconstituted tobacco sheets, especially tobacco fibres or reconstituted tobacco sheets which are impregnated with propylene glycol and/or glycerol. In this first embodiment, the solid smoking material is free from any tobacco or tobacco derived materials except for nicotine. However, the solid smoking material can comprise propylene glycol and glycerol as a wax or gel.

In order to load the electronic smoking device 1 with solid smoking material, the mouthpiece portion 16 with the receiving unit 3 therein is detached from the main body 17 of the electronic smoking device 1. Solid smoking material is then inserted into the receiving unit 3 within the mouthpiece portion 16, compressing the spring 28 with the piston 27 thereon into a biased state.

In some embodiments of an electronic smoking device 1 according to the invention, the positioning element 6 or the electronic smoking device 1 in general can comprise a moveable stopper (not shown). Such a moveable stopper, for example a moveable leverage, maintains the positioning element 6 in a biased state when the solid smoking material is inserted into the receiving unit 3 and releases the positioning element 6 when the mouthpiece portion 16 is reattached to the main body 17 or upon an actuation of a user. When the assembled electronic smoking device 1 is loaded with solid smoking material, the positioning element 6 decompresses and forces the solid smoking material towards or against the primary heating element 5.

In use, a user sucks on the mouthpiece portion 16 of the electronic smoking devices 1. This causes air to be drawn into the electronic smoking devices 1 via the air inlets 25 and to be drawn up via the airflow passage in the mouthpiece portion 16 towards the air inhalation port 24. The airflow is guided from the air inlets 25 around the receiving unit 3 towards the air inhalation port 24. The change in air pressure which arises is detected by the airflow sensor 22 which generates an electrical signal that is passed to the control electronics 21. In response to the signal, the control electronics 21 then proceed to activate the primary heating element 5. The heat generated by the heating element 5 causes the solid smoking material forced towards the primary heating element 5 to be first liquefied and then atomized, resulting in an aerosol which may comprise gaseous and liquid components within the airflow passage provided within the mouthpiece portion 16. As the user continues to suck on the mouthpiece portion 16 of the electronic smoking device 1, the aerosol is drawn up along the airflow passage and inhaled by the user sucking on the electronic smoking device 1. At the same time the control electronics 21 also activate the LED 20 causing the LED 20 to light up which is visible via the translucent end cap 18 mimicking the appearance of a glowing member at the end of a conventional cigarette. As the solid smoking material adjacent to the primary heating element 5 is converted into an aerosol, more solid smoking material contained within the receiving unit 3 is forced towards the primary heating element 5 and thus is available to be converted into an aerosol through a subsequent activation of the primary heating element 5.

It will also be appreciated that although the above description is illustrative of the structure and function of a typical electronic smoking device 1, variations also exist. Thus for example in some electronic smoking devices 1 the LED 20 is omitted. In some electronic smoking devices 1, the airflow sensor 22 may be placed adjacent the end cap 18 of the electronic smoking devices 1 rather than in the middle of the electronic smoking devices 1 as illustrated. Similarly, in some electronic smoking devices 1, the air inlets 25 may be placed at the distal end of the main body 17 of the electronic smoking devices 1 remote from the mouthpiece portion 16. In some electronic smoking devices 1 the airflow sensor 22 is omitted and instead a push button is provided which enables a user to activate the electronic smoking devices 1 manually rather than in response to the detection of a change in air flow or air pressure. Also in some electronic smoking devices 1 the constitution of the atomizer 23 and especially of the primary heating element 5 may be changed. Thus for example rather than having a heating coil 29, other configurations may be used such as providing a spiral shaped heating element in a cavity in the interior of the main body 17 or the mouthpiece portion 16 for atomization and generation of an aerosol by evaporating the solid smoking material.

An advantage of an electronic smoking device according to the invention is an improvement in handling of solid smoking material. A user intending to charge the electronic smoking device with a solid smoking material can easily insert solid smoking material into the receiving unit, for example by only using one hand, so no further tools for the insertion of the solid smoking material is needed. The positioning element automatically forces the solid smoking material inserted in the receiving unit towards the primary heating element which simplifies the refilling procedure. No leakage nicotine liqus is avoided due to the use of a solid smoking material.

Figure 2A:
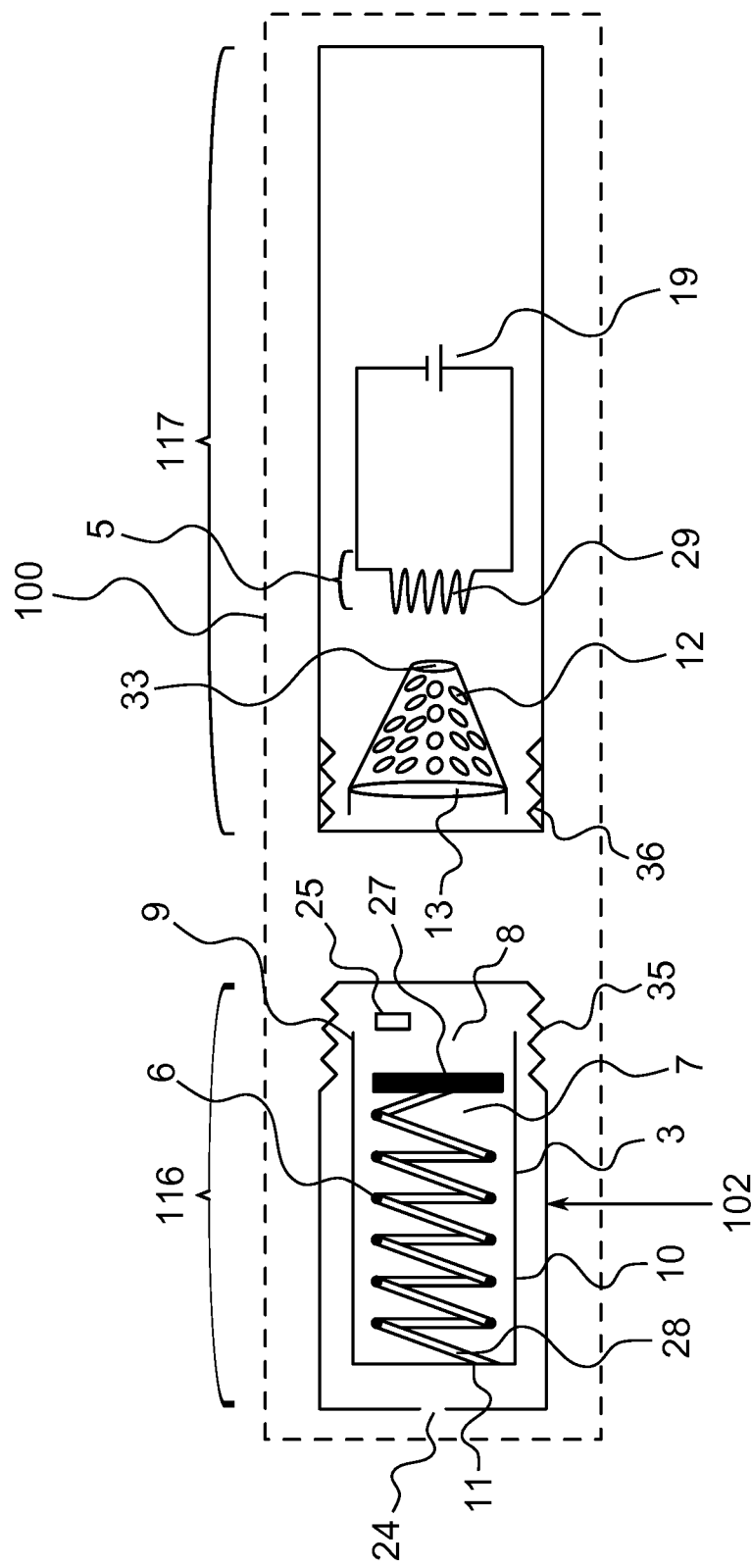
FIG. 2a is a schematic cross-sectional illustration of a second embodiment of an electronic smoking device according to the invention.

In FIG. 2a, a schematic cross-sectional illustration of a second embodiment of an electronic smoking device 100 according to the invention is shown. This second embodiment is substantially identical to the first embodiment as shown in FIG. 1 and as described hereinbefore. The components of the electronic smoking device 100 in FIG. 2a with reference signs which are identical to the respective reference signs shown in FIG. 1 will not be described further.

As in the case of the first embodiment, the second embodiment of an electronic smoking device 100 according to the invention also comprises a housing 102 which consists of a mouthpiece portion 116 and a corresponding main body 117. In this second embodiment, the mouthpiece portion 116 and the main body 117 are attached to each other via a screw fit connection. In more detail, the mouthpiece portion 116 comprises an external thread 35 which can be screwed to an internal thread 36 that is comprised by the main body 117 of the electronic smoking device 100.

In this second embodiment of the invention, the primary heating element 5 exemplarily comprises a heating coil 29. A heating coil 29 can generate a large amount of heat in a short time period with only a low amount of energy needed. The heating coil 29 is arranged within the main body 117 of the electronic smoking device 100. When the main body 117 and the mouthpiece portion 116 are attached to each other, the heating coil 29 of the primary heating element 5 is arranged adjacent to and in front of the open end 8 of the receiving unit 3. However, it is also possible to realize electronic smoking devices 100 according to the invention which comprise other primary heating elements 5. For example, such heating elements 5 can comprise a spiral shaped heating element or a heatable penetration means which will be described further below.

In this second embodiment of the invention, the electronic smoking device 100 further comprises a porous element 12 with an opening 13 which faces the open end 8 of the hollow body 7. The opening 13 of the porous element 12 exemplarily has a diameter which is substantially identical to the diameter of the open end 8 of the receiving unit 3. When the mouthpiece portion 116 is attached to the main body 117, the open end 8 exemplarily is in contact with the rim 9 of the open end 8 of the receiving unit 3. However, it is also possible to realize embodiments of electronic smoking devices 100 according to the invention which comprise porous elements 12 which are not in contact with the receiving unit 3 when the electronic smoking device 100 is fully assembled. Such porous elements 12 allow an improved concentration of solid smoking material on the primary heating element 5 and an improved atomization of solid smoking material via the pores of the porous element 12. The porous element 12 wicks liquefied solid smoking material towards the primary heating element 5. In this second embodiment of the invention, the porous element 12 comprises a capillary element, which is an element with at least one capillary tube. In this second embodiment of the invention, the capillary element exemplarily comprises a natural capillary sponge or a synthetic capillary sponge material. The capillarity of the sponge material causes pre heated smoking material to be sucked out of the porous element 12 and to be directly exposed to the primary heating element 5, enabling an additionally improved atomization of liquefied solid smoking material. In this second embodiment, the porous element 12 exemplarily has the conical shape of a nozzle, comprising the opening 13 and a second opening 33 on a side of the porous element 12 which is opposing the opening 13, wherein the diameter of the second opening 33 is smaller than the diameter of the opening 13. Such a shape of the porous element 12 allows an enforced concentration of solid smoking material on the primary heating element 5. However, it is also possible to realise porous elements 12 which are made of other materials and which have other shapes. For example, a porous element 12 can be made of a metal base material or of another material as for example ceramics which have a high thermal conductivity. Moreover, a porous element 12 can have any other shape, for example a cylindrical or a rectangular shape. Furthermore, a porous element 12 can be a solid piece of coated metal without any orifice. In FIG. 2a and the following Figures, the pores of the porous element 12 are shown as visible holes for the sake of a better understanding. However, in most embodiments, the pores are substantially smaller than shown in the Figures and are identical to the pores of a sponge.

As already described, the housing 102 of the electronic smoking device 100 comprises a mouthpiece portion 116 and a main body 117 which are attachable to one another, wherein the receiving unit 3 and the positioning element 6 are arranged within the main body 117 and wherein the primary heating element 5 is arranged within the mouthpiece portion 116. Also, the battery 19 is arranged within the main body 117. Such a housing 102 allows a handy exchangeability of solid smoking material and an eased refilling of the electronic smoking device 100 with the same. A user of such an electronic smoking device 100 can easily release the mouthpiece portion 116 from the main body 117 without having to change or affect any components within the main body 117. This makes it possible to refill the receiving unit 3 with a solid smoking material, only using his or her hands without further technical devices. However, it is also possible to realise embodiments of electronic smoking devices 100 according to the invention which comprise other housings 102 that can have a shape, design and functionality that fundamentally differ from the one shown in FIG. 2a. For example, a housing 102 can be made of one piece or comprise more than two pieces which are attachable to each other. Furthermore, a housing 102 can allow another kind of access to the receiving unit 3. Moreover, the components of the electronic smoking device 100, for example the receiving unit 3, the positioning element 6, the primary heating element 5, the porous element 12 or the battery 19 can be arranged in another kind within an electronic smoking device 100 according to the invention.

In this second embodiment of the invention, due to the arrangement of the receiving unit 3 within the electronic smoking device 100, air that is sucked from the air inlets 25 to the air inhalation port 24 within the mouthpiece portion 116 is forced to flow around the receiving unit 3 through a passage which is given between the side walls 10 of the receiving unit 3 and the housing 102 of the electronic smoking device 100. However, it is also possible to realize other arrangements of receiving units 3 within electronic smoking devices 100 according to the invention which determine other airflow passages within the device 100. In FIG. 2a, a first air inlet 25 is shown within the mouthpiece portion 116 of the electronic smoking device 100, wherein a second air inlet 25 is arranged within the main body 117 which in FIG. 2a is hidden behind the porous element 12 and therefore not shown. When the mouthpiece portion 116 and the main body are attached to each other via the screw fit connection, the first and second air inlets 25 are aligned so that air can enter the electronic smoking device 100.

Figure 2B:
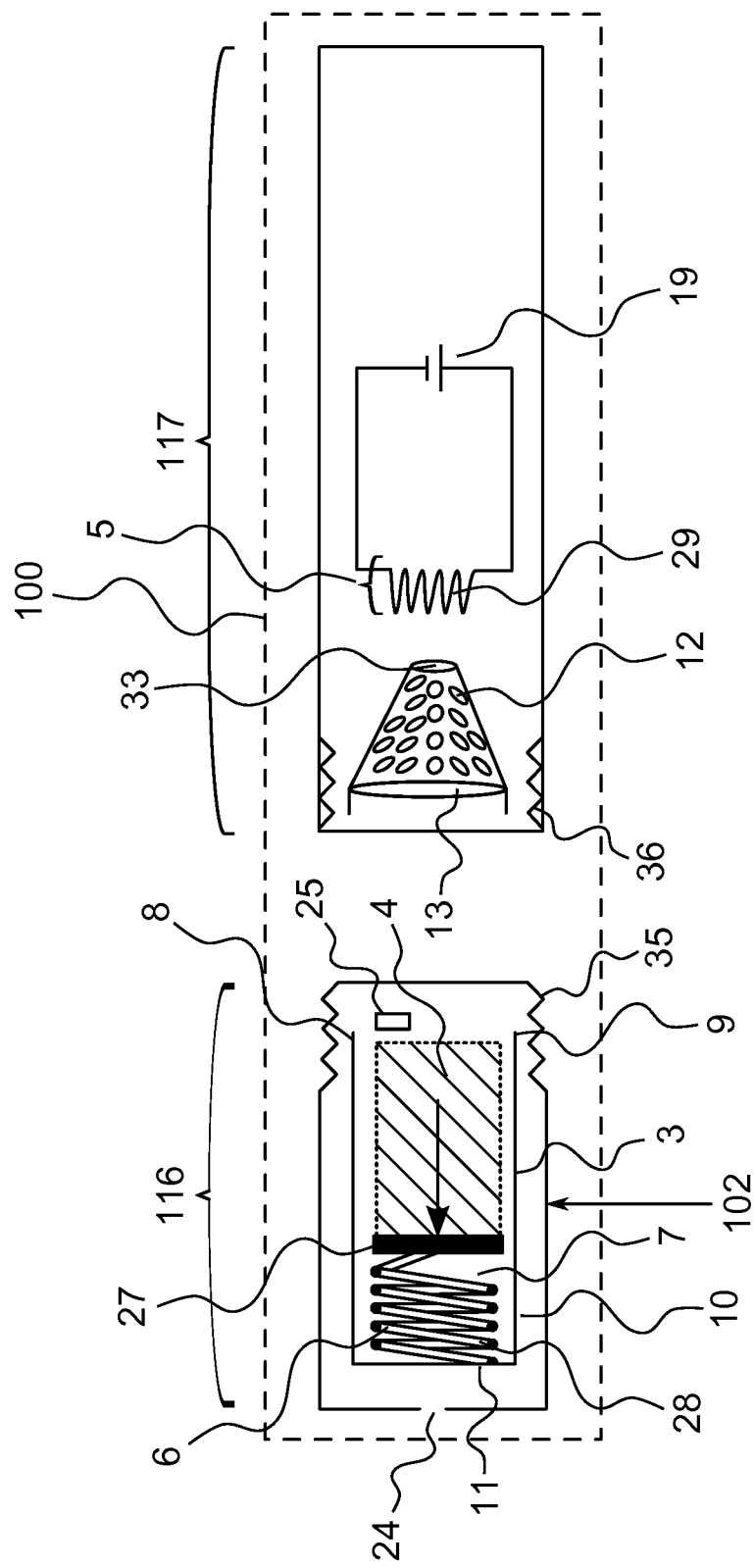
FIGS. 2b and 2c is a schematic cross-sectional illustration of the second embodiment of the electronic smoking device according to the invention which is pre-charged with a solid smoking material.
Figure 2C:
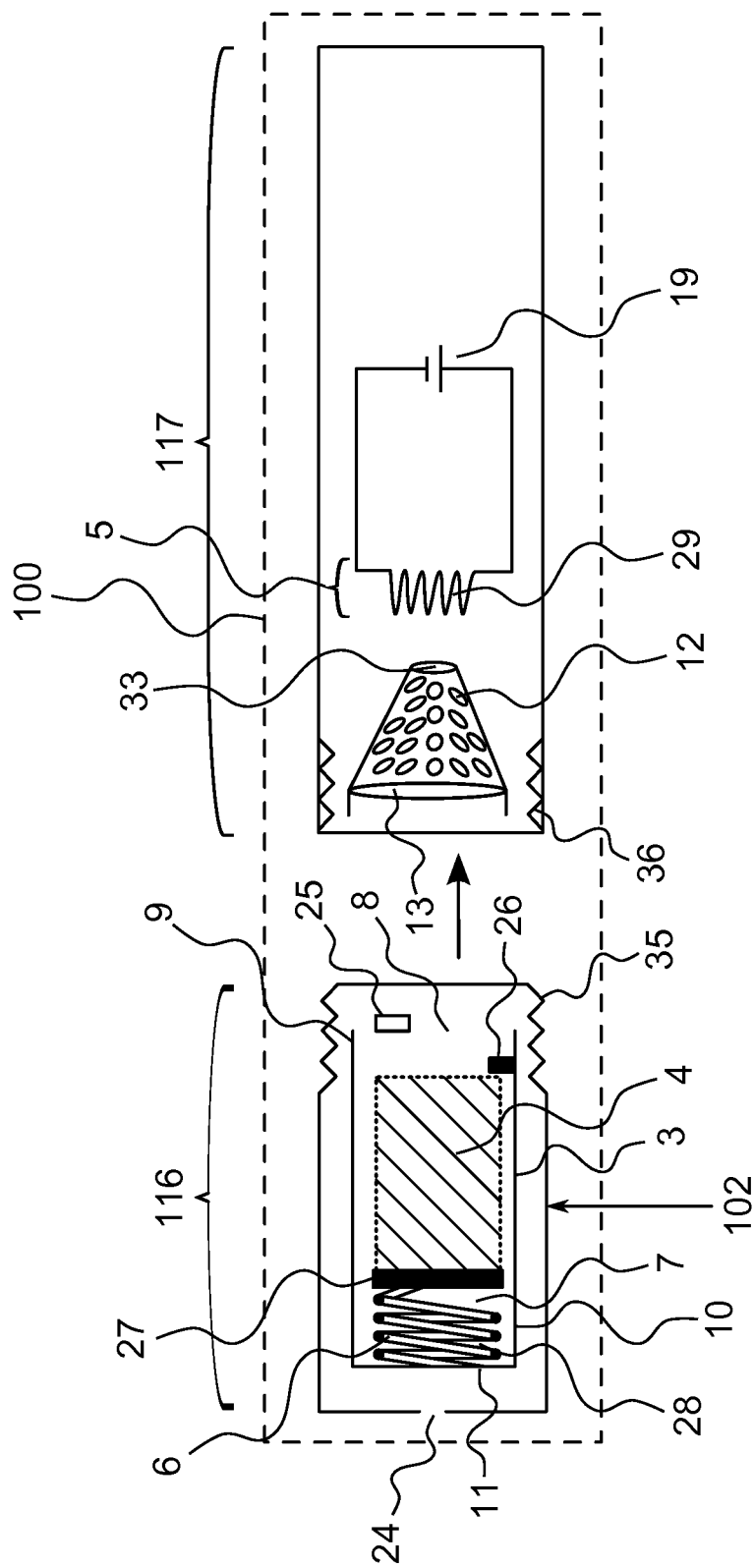

FIGS. 2b and 2c show a schematic cross-sectional illustration of the second embodiment of the electronic smoking device 100 according to the invention, wherein solid smoking material 4 is provided within the receiving unit 3. FIG. 2b shows how solid smoking material 4 is inserted into the receiving unit 3: When the mouthpiece portion 116 is released from the main body 117, the solid smoking material 4 is inserted into the receiving unit 3, for example using one hand to hold the mouthpiece portion 116 while the solid smoking material 4 is inserted with the other hand. By inserting the solid smoking material 4 into the receiving unit 3, the positioning element 6 for forcing solid smoking material 4 inserted in the receiving unit 3 towards the primary heating element 5, in this second embodiment the spring 28 with the piston 27 attached thereto, is compressed. The direction of compression is indicated by an arrow.

FIG. 2c shows the positioning element 6 in a fully compressed state and the solid smoking material 4 in a fully inserted state. In this second embodiment of the invention, the receiving unit 3 optionally further comprises a moveable stopper 26 which in this second embodiment exemplarily is realized as a moveable leverage. The moveable stopper 26 is adapted to snap out of a sidewall 10 of the receiving unit 3 as soon as the solid smoking material 4 is fully inserted into the receiving unit 3. The moveable stopper 26 can comprise a mechanical system (not shown) which for example can have a spring 28 which is arranged in a cavity within the receiving unit 3, causing the moveable stopper 26 to snap out of the side wall 10 as soon as the solid smoking material 4 is fully inserted into the receiving unit 3. The moveable stopper 26 prevents the solid smoking material 4 to be pushed, pulled or forced out of the receiving unit 3 by the positioning element 6 in a state of the electronic smoking device 100 in which the mouthpiece portion 116 is released from the main body 117. When the mouthpiece portion 116 is (re-)attached to the main body 117, the attachment forces the moveable stopper 26 to move out of the direction in which the solid smoking material 4 is forced by the positioning element 6, thereby releasing the solid smoking material 4. For this purpose, further mechanical components, electrical components, hydraulic components or other components (not shown) can be arranged within the electronic smoking device 100. In this second embodiment of the invention, a mechanical component (not show) is exemplarily arranged within the main body 117 of the electronic smoking device 100. In more detail, the mechanical component is arranged on the porous element 12 which physically pushes the moveable stopper 26 back into the side wall 10 as soon as the mouthpiece portion 116 is (re-)attached to the main body 117. However, it is also possible to realize embodiments of electronic smoking devices 100 which comprise other means to hold back solid smoking material 4 inserted into the receiving unit 3 as long as the mouthpiece portion 116 and the main body 117 are not attached to each other. Furthermore, a moveable stopper 26 as described hereinbefore does not have to be arranged on or within a side wall 10 of the electronic smoking device 100. It also can be arranged anywhere else on or in the receiving unit 3 or adjacent to the receiving unit 3. Furthermore, it is also possible to realize embodiments of electronic smoking devices 100 which do not comprise such means and which do not comprise a moveable stopper 26 as shown in FIG. 2c.

Figure 3:
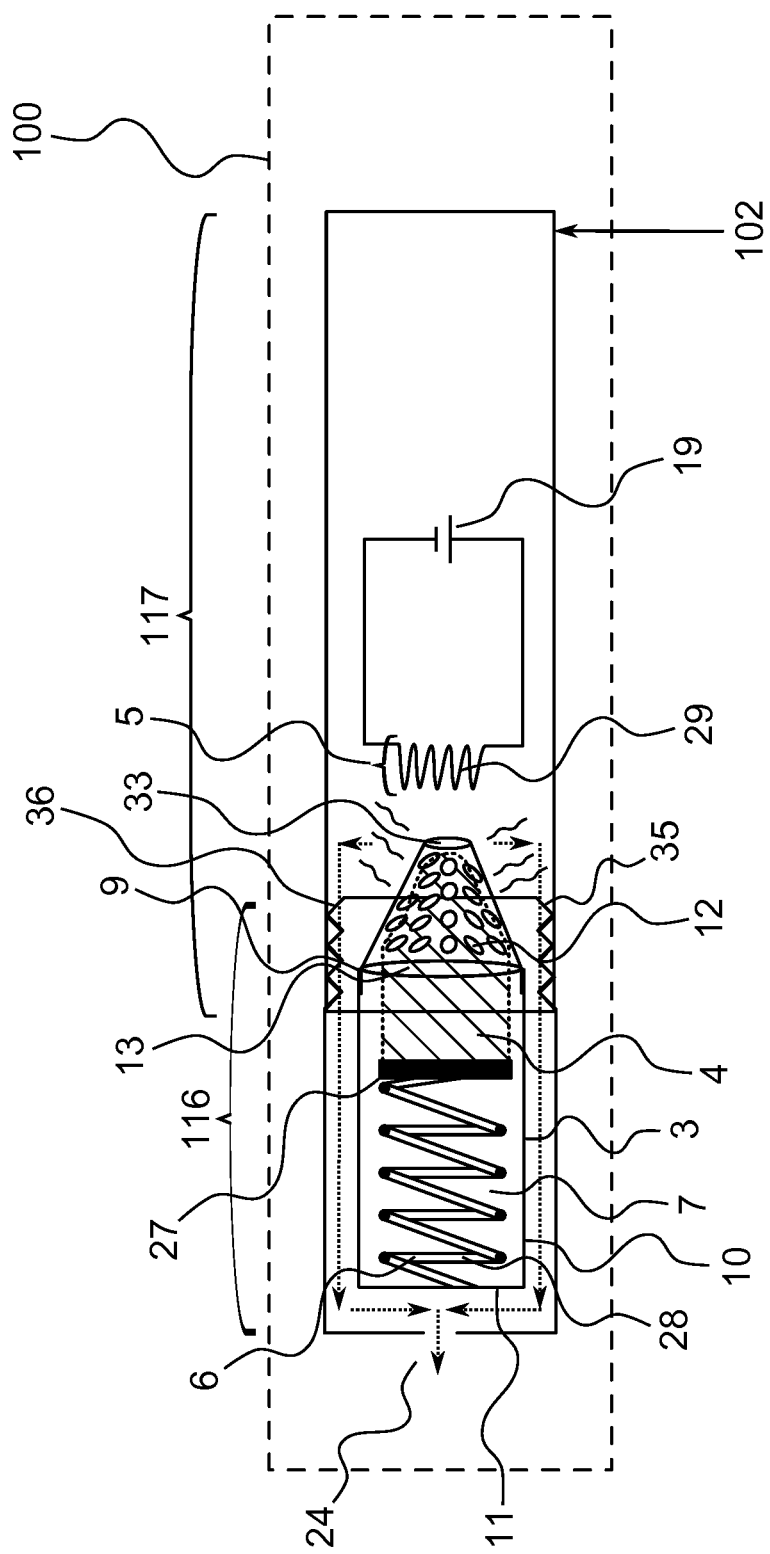
FIG. 3 is a schematic cross-sectional illustration of the second embodiment of the electronic smoking device according to the invention in an assembled and activated state.

FIG. 3 is a schematic cross-sectional illustration of the second embodiment of the electronic smoking device 100 according to the invention in an assembled and activated state. FIG. 3 shows the electronic smoking device 100 as shown in FIGS. 2a to 2c in use. The mouthpiece portion 116 with the filled receiving unit 3 is attached to the main body 117 of the electronic smoking device 100. The moveable stopper 26 has released the solid smoking material 4 so that the positioning element 6, the spring 28, decompresses and forces the solid smoking material 4 towards the open end 8 of the receiving unit 3 and towards the primary heating element 5. When the mouthpiece portion 116 is (re-)attached to the main body 117, the opening 13 of the porous element 12 is in contact with the rim 9 of the open end 8 of the receiving unit 3. The positioning element 6 pushes the solid smoking material 4 into the porous element 12. Due to the heat radiated by the primary heating element 5, the solid smoking material 4 closest to the primary heating element 5 starts to melt, wherein solid smoking material 4 is firstly liquefied, and the liquefied material is wicked through the porous element 12 towards the primary heating coil 5 and is then atomized by the primary heating element 5 as usually done within electronic cigarettes containing an atomizer and a liquid smoking material. The melting combined with the pressure or force which the positioning element 6 applies to the solid smoking material 4 causes the solid smoking material 4 to reduce its diameter at its tip, where it is in contact with the porous element 12, allowing to further push the solid smoking material 4 into the porous element 12. In other words, the solid smoking material is primed into the porous element 12 where it melts so that the porous element 12 is drenched in liquid. If in such a state, the primary heating element 5 is switched off, the liquid resolidifies to solid smoking material.

Solid smoking material 4 which has been liquefied and then atomized can be sucked to the air inhalation port 24 by the user. In use, atomized solid smoking material 4 flows along the side walls 10 of the receiving unit 3 and through the air inhalation port 24 as indicated in FIG. 3 by arrows.

Figure 4:
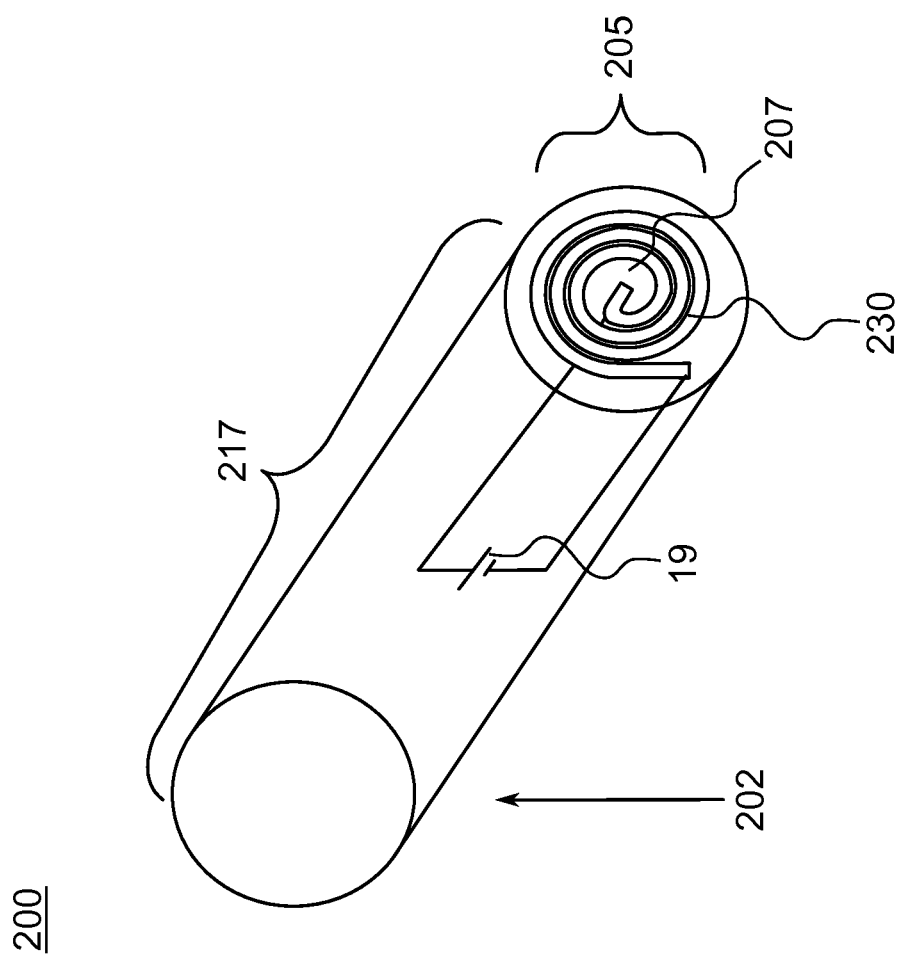
FIG. 4 is a schematic illustration of a third embodiment of an electronic smoking device according to the invention.

FIG. 4 is a schematic illustration of a third embodiment of an electronic smoking device 200 according to the invention. The third embodiment is substantially identical to the second embodiment as shown in FIGS. 2a to 3 and as described hereinbefore. However, in FIG. 4, some of the components of the electronic smoking device 100 as shown in FIGS. 2a to 3 are not shown but nevertheless form a part of the third embodiment of an electronic smoking device 200 according to the invention as shown in FIG. 4. In more detail, in FIG. 4, only some components of the main body 217 of the electronic smoking device 200 of the third embodiment are schematically illustrated. FIG. 4 shows the main body 217 as a part of the housing 202 of the third embodiment of an electronic smoking device 200 according to the invention, comprising a primary heating element 205 which differs from the primary heating element 5 as described hereinbefore. In this third embodiment of the invention, the primary heating element 205 comprises a spiral shaped heating element 230. Using such a spiral shaped heating element 230, the solid smoking material can directly be forced through the spiral shaped heating element 230, so that a porous element advantageously can be omitted which reduces the manufacturing costs of the electronic smoking device 200. When the windings of the spiral shaped heating element 230 are arranged in parallel to each other, so within a plane, the space needed for the primary heating element 205 is additionally substantially reduced. In this third embodiment of the invention, the spiral shaped heating element 230 is exemplarily directly connected to the battery 19 within the main body 217. The main body 217 of this third embodiment for example can be attached to the mouthpiece portion 116 of the second embodiment of the electronic smoking device 100 as shown in FIGS. 2a to 3. In such a combination, when the mouthpiece portion 116 is charged with solid smoking material, the positioning element 6 forces the solid smoking material towards and through the sprial shaped heating element 230. For instance, as shown in FIG. 4, the spiral heating element 205 is provided with a void 207 in its centre. This solid smoking material 4 could be forced into this void 207 melting and atomizing therein. Thus, the solid smoking material 4 would be in better contact with the heating element 205 improving the atomization process. In another embodiment, between each pair of neighbouring spiral windings, a gap may be formed. In this case, the solid smoking material 4 could not only be pushed into the centre void 207 of the heating element 205, but into each pair of neighbouring windings further improving the contact area between the solid smoking material 4 and the heating element 205 and thus further improving the atomization process.

Figure 5:
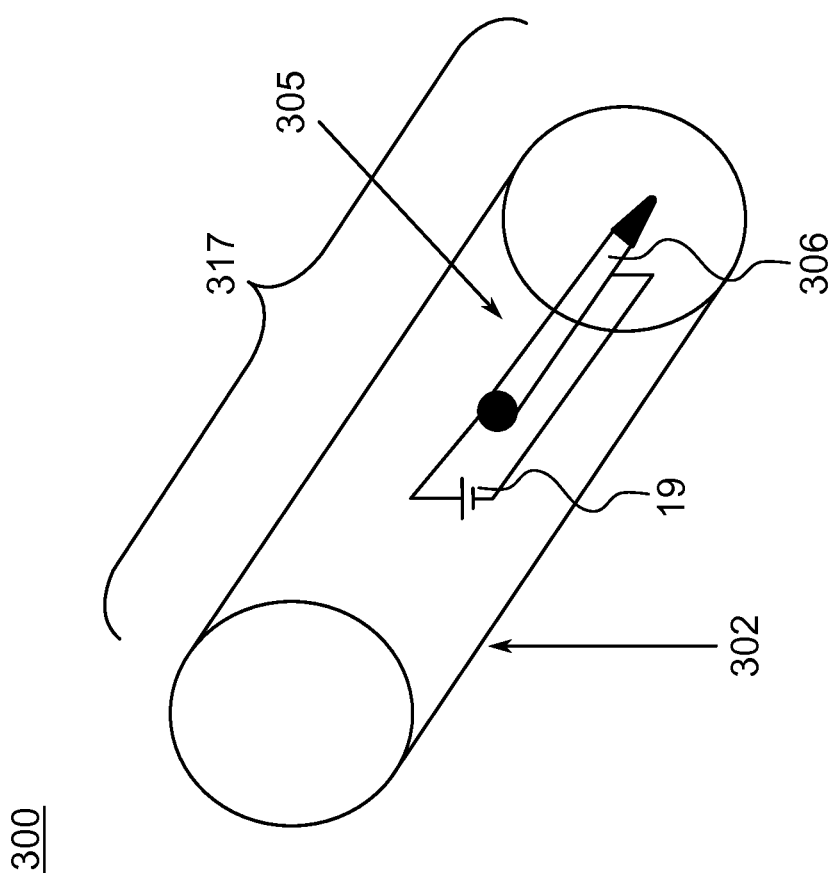
FIG. 5 is a schematic illustration of a fourth embodiment of an electronic smoking device according to the invention.

FIG. 5 is a schematic illustration of a fourth embodiment of an electronic smoking device 300 according to the invention. The fourth embodiment is substantially identical to the second embodiment as shown in FIGS. 2a to 3 and as described hereinbefore. However, in FIG. 5, some of the components of the electronic smoking device 100 as shown in FIGS. 2a to 3 are not shown but nevertheless form a part of the fourth embodiment of an electronic smoking device 300 according to the invention as shown in FIG. 5. In more detail, in FIG. 5, only some components of the main body 317 of the electronic smoking device 300 of the fourth embodiment are schematically illustrated. FIG. 5 shows the main body 317 as a part of the housing 302 of the fourth embodiment of an electronic smoking device 300 according to the invention, comprising a primary heating element 305 which differs from the primary heating element 5, 205 as described hereinbefore. In this fourth embodiment of the invention, the primary heating element 305 comprises a heatable penetration means 306 which is adapted to penetrate solid smoking material 4 forced towards the primary heating element 305. In this fourth embodiment of the invention, the heatable penetration means 306 exemplarily has the shape of a nail and is made of a metal. The nail is directly electrically connected to the battery 19 within the main body 317. However, the primary heating element 305 can have any other shape, can be of any other electrically and thermally conductive material and can also only be indirectly connected to the battery 19.

In this fourth embodiment, the primary heating element 305 is adapted to pierce solid smoking material 4 which is forced towards the primary heating element 305 and through the open end 8 of the receiving unit 3 by the positioning element 6. When the mouthpiece portion 116 of the second embodiment as shown in FIGS. 2a to 3 and the main body 317 of the fourth embodiment as shown in FIG. 5 are attached to one another, the primary heating element 305 pierces or penetrates the solid smoking material 4. Upon heating and insertion of the penetration means 306 into the solid smoking material 4, the penetration means 306 liquefies and atomizes the solid smoking material 4 from an inside of the solid smoking material 4.

Figure 6:
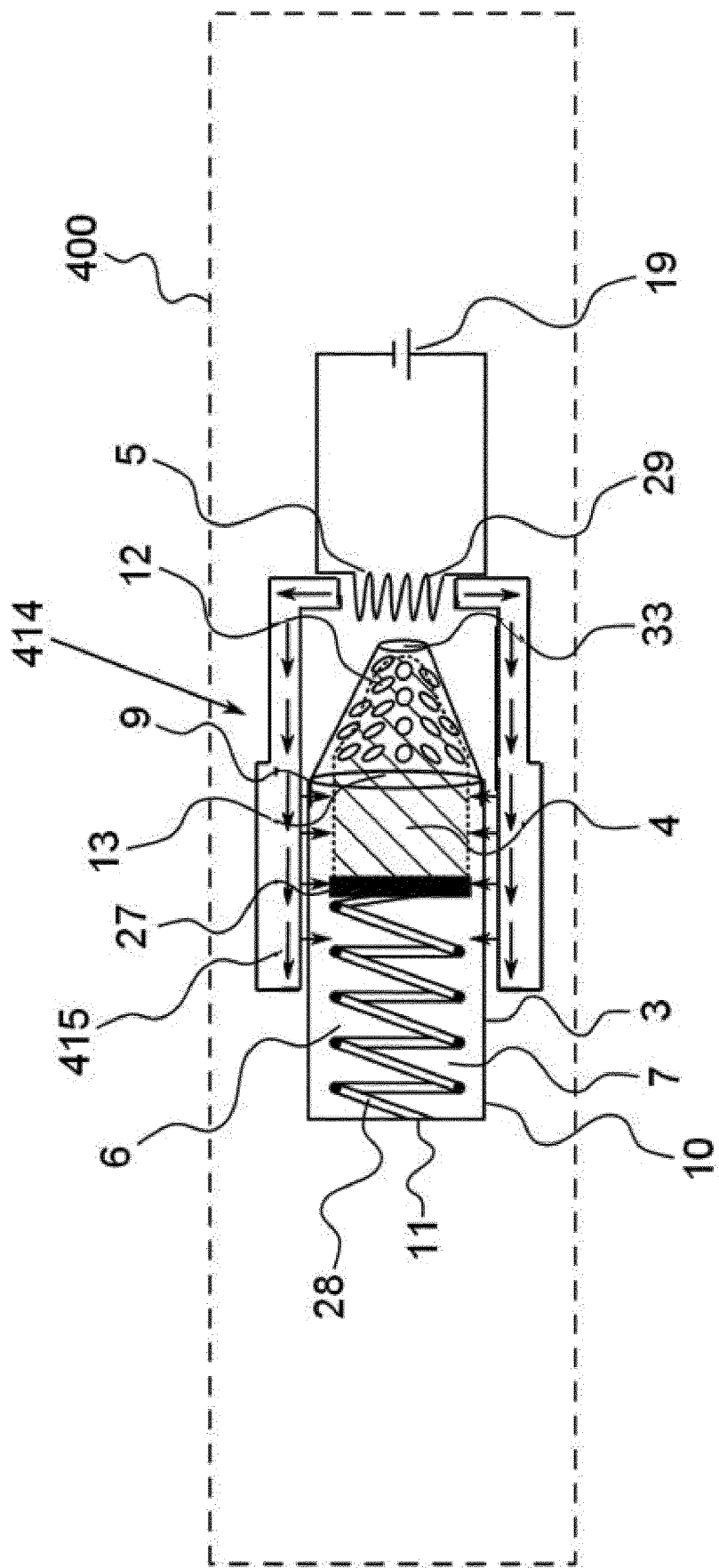
FIG. 6 is a schematic illustration of a fifth embodiment of an electronic smoking device according to the invention.

FIG. 6 is a schematic illustration of a fifth embodiment of an electronic smoking device 400 according to the invention. The fifth embodiment is substantially identical to the second embodiment as shown in FIGS. 2a to 3 and as described hereinbefore. The components of the electronic smoking device 400 in FIG. 6 with reference signs which are identical to the respective reference signs shown in FIGS. 2a to 3 will not be described further hereinafter. However, the given description related to the components with these reference signs is also applicable to the components with identical reference signs shown in FIG. 6. Furthermore, in FIG. 6, some of the components as for example the housing 102 of the electronic smoking device 100 as shown in FIGS. 2a to 3 are not shown but nevertheless form a part of the fifth embodiment of an electronic smoking device 400 according to the invention as shown in FIG. 6.

Figure 7:
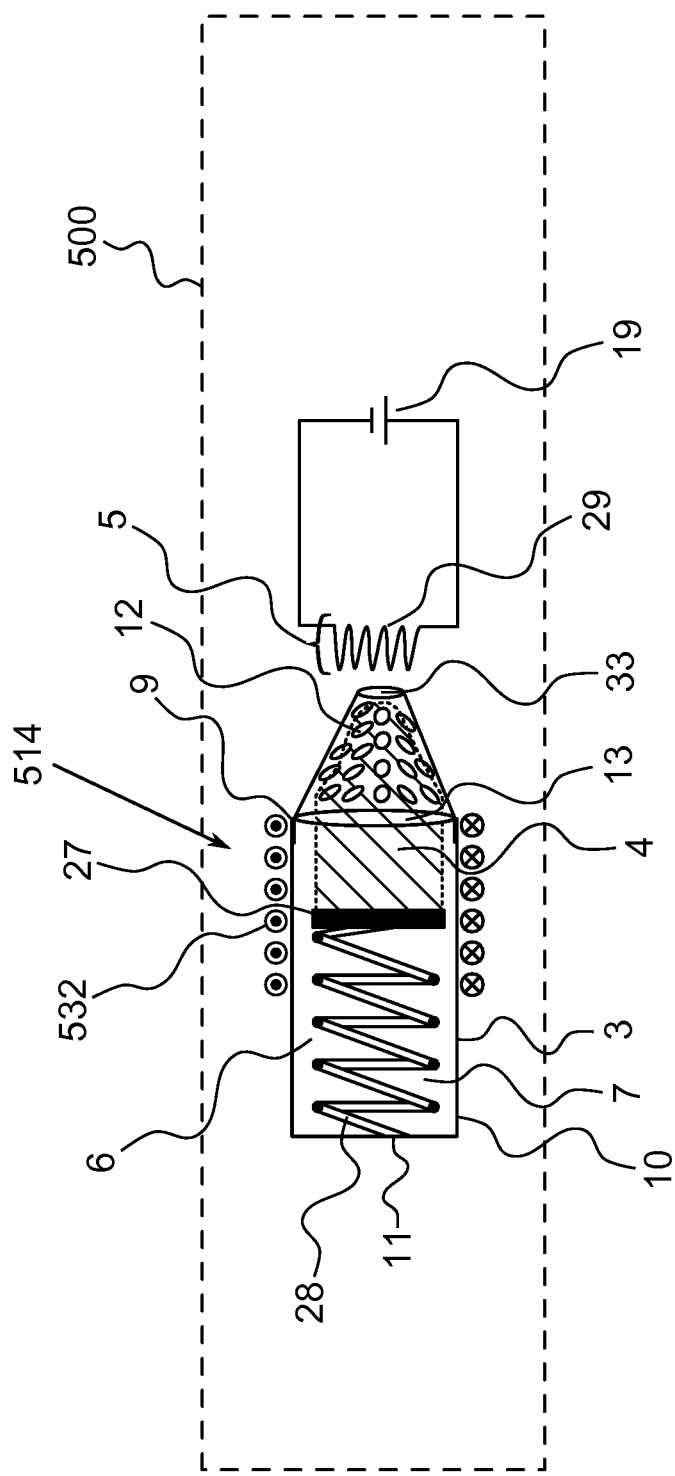
FIG. 7 is a schematic illustration of a sixth embodiment of an electronic smoking device according to the invention.

In this fifth embodiment, the electronic smoking device 400 further comprises a secondary heating element 414 adapted to pre-heat solid smoking material 4 within the receiving unit 3. With such a secondary heating element 414, solid smoking material 4 inserted into the receiving unit 3 can be atomized faster which increases the enjoyment of puffing on the device 400. In this fifth embodiment, the secondary heating element 414 exemplarily is a thermal conductor element which is arranged adjacent to the receiving unit 3 and the primary heating element 5 and which is adapted to conduct heat from the primary heating element 5 to the receiving unit 3. With such an embodiment, heat can easily be harvested from the primary heating element 5 and be transported to the receiving unit 3, especially to the side walls 10 of the receiving unit 3, in order to pre-heat solid smoking material 4 therein. This is achieved without using a second electrical consumer to the battery 19 which enables a reduction of the overall energy consumption of the electronic smoking device 400 and simultaneously increases the energy efficiency of the same. In this fifth embodiment of the invention, the thermal conductor element comprises two metal plates 415 which are arranged adjacent to the side walls 10 of the receiving unit 3. With such metal plates 415, the heat can be distributed over substantially the whole area of the side walls 10 of the receiving unit 3, allowing an improved pre-heating of solid smoking material 4 inserted in the receiving unit 3. The metal plates 415 can extend along the whole length and/or width or along a fraction of the length and/or the width of the side walls 10 of the receiving unit 3. In this fifth embodiment, the metal plates 415 exemplarily fully enclose the receiving unit 3, the metal plates 415 being joined together in an upper portion (not shown). In FIG. 6, the transportation of heat from the primary heating element 5 to the receiving unit 3 via the thermal conductor element is indicated by arrows. FIG. 7 is a schematic illustration of a sixth embodiment of an electronic smoking device 500 according to the invention. The sixth embodiment is substantially identical to the second embodiment as shown in FIGS. 2a to 3 and as described hereinbefore. The components of the electronic smoking device 500 in FIG. 7 with reference signs which are identical to the respective reference signs shown in FIGS. 2a to 3 will not be described further hereinafter. However, the given description related to the components with these reference signs is also applicable to the components with identical reference signs shown in FIG. 7. Furthermore, in FIG. 7, some of the components as for example the housing 102 of the electronic smoking device 100 as shown in FIGS. 2a to 3 are not shown but nevertheless form a part of the sixth embodiment of an electronic smoking device 500 according to the invention as shown in FIG. 7.

In this sixth embodiment, the electronic smoking device 500 also further comprises a secondary heating element 514 adapted to pre-heat solid smoking material 4 within the receiving unit 3. However, in this sixth embodiment, the secondary heating element 514 is an electrically heatable device arranged adjacent to the receiving unit 3 and not a passive thermal conductor element. With such an electrically heatable device, large amounts of heat can be quickly generated and provided to the receiving unit 3, without the primary heating element 5 having to be powered. Furthermore, such electrically heatable devices can reach high temperatures and are decoupled from the primary heating element 5. Therefore, it is also possible to precisely adjust the heat generation of the primary and secondary heating elements 5, 514 to one another. For example, it is possible to first pre-heat solid smoking material 4 within the receiving unit 3 via the secondary heating element 514 while the primary heating element 5 remains in an off-state. After a predefined time-period has passed, the secondary heating element 514 can be turned off and the primary heating element 5 is turned on, thereby ameliorating the overall energy efficiency of the device 500.

In this sixth embodiment of the electronic smoking device 500 according to the invention, the secondary heating element 514 comprises a heating coil 532 which radially encloses a part of the receiving unit 3. However, the second heating coil 532 can also radially enclose the receiving unit 3 over its total length. In such an embodiment, the pre-heating of solid smoking material 4 can be controlled precisely and the time needed to consume the solid smoking material 4 can be further reduced. Furthermore, a pre-heating of solid smoking material 4 can be completely decoupled from the primary heating element 5. In this sixth embodiment, the receiving unit 3 is arranged within the heating coil 532 which is comprised by the secondary heating element 514. Therefore, the windings of the heating coil 532 of the secondary heating element 514 extend along the side walls 10 of the receiving unit 3. In this sixth embodiment of the invention, the secondary heating element 514 is exemplarily electrically connected to the battery 19 (not shown). The electrical connection can have a switching means therein that can be actuated by a user, switching on or off the secondary heating element 514. Furthermore, such a switching means can be omitted and the secondary heating element 514 can be coupled to the primary heating element 5, so that an actuation of the primary heating element 5 also actuates the secondary heating element 514.

Moreover, it is also possible to realize embodiments of electronic smoking devices 500 according to the invention with secondary heating elements 514 that fundamentally differ from the secondary heating element 514 as shown in FIG. 7. Moreover, a secondary heating element 514 used in an electronic smoking device 500 according to the invention is not limited to be formed in the shape of a second heating coil 532. It also can be realised as a heating plate or any other heating body. The secondary heating element 514 may also have the shape of a cylinder enclosing at least a part of the solid smoking material 4 therein.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS

| | |
|---|---|
| 1, 100, 200, 300, 400, 500 | electronic smoking device |
| 2, 102, 202, 302 | housing |
| 3 | receiving unit |
| 4 | solid smoking material |
| 5, 205, 305 | primary heating element |
| 6 | means |
| 7 | hollow body |
| 8 | opening |
| 9 | rim |
| 10 | side wall |
| 11 | rear wall |
| 12 | porous element |
| 13 | opening |
| 16, 116 | mouthpiece portion |
| 17, 117, 217, 317 | main body |
| 18 | end cap |
| 19 | battery |
| 20 | light emitting diode (LED) |
| 21 | control electronics |
| 22 | airflow sensor |
| 23 | atomizer |
| 24 | air inhalation port |
| 25 | air inlet |
| 26 | moveable stopper |
| 27 | piston |
| 28 | spring |
| 29 | heating coil |
| 33 | second opening |
| 35 | external thread |
| 36 | internal thread |
| 207 | void |
| 230 | spiral shaped heating element |
| 306 | heatable penetration means |
| 414, 514 | secondary heating element |
| 415 | metal plate |
| 532 | second heating coil |

The invention claimed is:

1. An electronic smoking device, comprising:
a housing;
a receiving unit arranged within the housing operable to receive a solid smoking material suited for aerosol generation, wherein the receiving unit includes a hollow body having an open end;
a primary heating element arranged adjacent to the receiving unit and adapted to liquefy the solid smoking material to provide a liquefied smoking material, wherein the primary heating element is further adapted to atomize the liquefied smoking material;
a positioning element for forcing the solid smoking material in the receiving unit towards the primary heating element; and
a porous element located between the primary heating element and the open end of the hollow body.

2. The electronic smoking device of claim 1, wherein the porous element comprises a capillary element.

3. The electronic smoking device of claim 1, wherein the porous element has a shape of a nozzle or a cone.

4. The electronic smoking device of claim 1, wherein the positioning element comprises at least one spring.

5. The electronic smoking device of claim 4, wherein the at least one spring is attached to the receiving unit and adapted to force the solid smoking material in the receiving unit towards the open end of the hollow body.

6. The electronic smoking device of claim 1, wherein the primary heating element comprises a heating coil.

7. The electronic smoking device of claim 1, wherein the primary heating element is a spiral shaped heating element.

8. The electronic smoking device of claim 1, wherein the primary heating element is adapted to penetrate the solid smoking material forced towards the primary heating element.

9. The electronic smoking device of claim 1, further comprising a secondary heating element adapted to pre-heat the solid smoking material within the receiving unit.

10. The electronic smoking device of claim 9, wherein the secondary heating element comprises a thermal conductor element arranged adjacent to the receiving unit and the primary heating element and which is adapted to conduct heat from the primary heating element to the receiving unit.

11. The electronic smoking device of claim 1, wherein the open end has a rim and wherein the receiving unit further comprises a side wall extending from the rim of the open end and a rear wall.

12. The electronic smoking device of claim 10, wherein the thermal conductor element comprises at least one metal plate which is arranged adjacent to the side wall of the receiving unit.

13. The electronic smoking device of claim 9, wherein the secondary heating element is an electrically heatable device arranged adjacent to the receiving unit.

14. The electronic smoking device of claim 9, wherein the secondary heating element comprises a heating coil which radially encloses the receiving unit at least in part.

15. The electronic smoking device of claim 1, wherein the housing comprises a mouthpiece portion and a main body which are attachable to one another, wherein the receiving unit and the positioning element are arranged within the main body, and wherein the primary heating element is arranged within the mouthpiece portion.

16. The electronic smoking device of claim 1, wherein the solid smoking material is made at least in part of a wax, a gel, or a combination thereof.

* * * * *